United States Patent [19]

Brandestini

[11] 4,112,740

[45] Sep. 12, 1978

[54] METHOD AND APPARATUS FOR DETERMINING A CHANGE OF THE FLOW STATE OF FLOWABLE SUBSTANCES FROM ITS STATIC STATE TO ITS FLOWING STATE OR VICE VERSE

[75] Inventor: Marco Brandestini, Zurich, Switzerland

[73] Assignee: Contraves AG, Zurich, Switzerland

[21] Appl. No.: 816,715

[22] Filed: Jul. 18, 1977

[30] Foreign Application Priority Data

Jan. 13, 1977 [CH] Switzerland ............................ 392/77

[51] Int. Cl.$^2$ .......................................... G01N 29/02
[52] U.S. Cl. ........................................ 73/53; 73/64.1; 340/608
[58] Field of Search ..................... 73/53, 64.1, 194 A; 340/239 R, 258 A

[56] References Cited

U.S. PATENT DOCUMENTS

| | | | |
|---|---|---|---|
| 3,925,773 | 12/1975 | Green | 340/258 A |
| 4,003,045 | 1/1977 | Stockdale | 340/258 A |
| 4,012,730 | 3/1977 | Nicholls | 340/258 A |
| 4,014,650 | 3/1977 | Sigelmann | 73/64.1 X |

*Primary Examiner*—Charles A. Ruehl
*Attorney, Agent, or Firm*—Werner W. Kleeman

[57] ABSTRACT

A method and apparatus for determining a change of the flow state of a flowable substance by transmitting ultrasonic or ultrasound waves of constant frequency to a spatial region of the substance, receiving ultrasonic waves backscattered by the substance, converting the backscattered ultrasonic waves into a primary signal which is amplitude- and phase-modulated in accordance with the backscattering and demodulating the primary signal in order to obtain a modulation signal. This modulation signal can be divided into a spectrum of signal components of different frequency and possessing pseudo periods which are defined as the time intervals between successive momentary values of the modulation signal, such momentary values corresponding to one another. The time duration corresponding to a predetermined number of pseudo periods is compared with a predetermined time duration.

18 Claims, 5 Drawing Figures

METHOD AND APPARATUS FOR DETERMINING A CHANGE OF THE FLOW STATE OF FLOWABLE SUBSTANCES FROM ITS STATIC STATE TO ITS FLOWING STATE OR VICE VERSE

BACKGROUND OF THE INVENTION

The present invention relates to a new and improved method of, and apparatus for, determining a change of the flow state or condition of a flowable or fluent substance by means of ultrasonic energy or ultrasound.

In particular, the method for determining the change of such flow state contemplates transmitting ultrasonic or ultrasound waves of substantially constant frequency to a spatial region or specified volume of the substance, receiving the ultrasonic waves which are backscattered by the substance, converting the same into an amplitude- and phase-modulated primary signal corresponding to the backscattering and demodulating the primary signal in order to obtain a modulation signal which can be divided into a spectrum of signal components of different frequency and possessing pseudo periods which are defined as the time spacing between successive momentary values of the modulation signal and corresponding to one another. Further, the apparatus for determining the flow condition of a fluent or flowable substance is of the type comprising a signal generator for generating a reference signal of substantially constant frequency, an ultrasonic transmitter arranged in series with the signal generator for transmitting ultrasonic waves corresponding to the reference signal to a spatial region or specified volume of the substance. Further, there is provided an ultrasonic receiver for receiving ultrasonic or ultrasound waves backscattered at the substance and for converting the same into an amplitude- and phase-modulated primary signal corresponding to the backscattering. A demodulator serves for obtaining a modulation signal from the primary signal and an analyser serves for detecting signal components of the modulation signal.

Such type method and apparatus have already been disclosed in the publication of Shung, Sigelmann and Schmer in "IEEE Transactions of Biomedical Engineering" BME-22/4 (No. 6/1975) pages 334–337, and specifically in conjunction with the determination of the coagulation time of blood. Ultrasonic or ultrasound waves are backscattered or scattered both at the blood samples and also at the plasma samples, indicating that the ultrasonic waves are not exclusively scattered by the blood cells, rather also by other type of inhomogeneities of the sample liquid, for instance by micelles, density differences and the like. With the selected ultrasonic frequency every incoherent movement of the examined sample liquid, caused for instance by a turbulent state, convection or by Brownian movement, brings with it a modulation of the backscattered ultrasonic waves, and specifically a randomly controlled amplitude- and phase-modulation having a respective statistical distribution according to Rayleigh. From the aforementioned publication it is known to detect amplitude values of the backscattered ultrasonic waves as squared mean values, i.e., there is measured the intensity of the backscattered ultrasonic waves which prevails over a predetermined time duration. If there does not occur any incoherent movement in the sample liquid, then the measured intensity is essentially constant, its value corresponds to the backscattering of the ultrasonic waves by the static or stationary sample liquid and therefore does not amount to null. On the other hand, if incoherent movements arise in the sample liquid, then the intensity of the backscattered ultrasonic waves fluctuates about a mean value.

What is disadvantageous with the prior art measuring technique is that the point in time of transition from the incoherent to the coherent flow state or condition can only be determined inaccurately. Furthermore, this fact has been expressly mentioned in such aforementioned publication. During the formation of the intensity value as the squared mean value of the amplitude there occurs a suppression of high frequencies which thereafter cannot be rescinded. Consequently, the measuring technique is associated with inaccuracies or ambiguities in the time determination, and such constitutes an obstacle for automation of the measuring technique. In the aforementioned prior art publication there is not proposed any solution for overcoming such drawback.

SUMMARY OF THE INVENTION

Therefore, with the foregoing in mind it is a primary object of the present invention to provide a new and improved method of, and apparatus for, determining the a change of the flow state of a flowable substance which effectively overcomes the drawbacks of the heretofore known measuring technique and additionally renders possible automation of such measuring technique.

Still a further significant object of the present invention aims at the provision of a new and improved construction of apparatus for determining a change of the flow state of a flowable material or substance in an extremely accurate, relatively simple and reliable manner, which apparatus is easy to use, economical to construct, highly reliable in operation, and not readily subject to malfunction or breakdown.

Yet a further object of this invention is to provide a novel method of determining a change of the flow state or condition of a flowable substance with greater accuracy than heretofore possible, while eliminating the drawbacks of the prior art proposal discussed above.

Now in order to implement these and still further objects of the invention, which will become more readily apparent as the description proceeds, the method of the present development for determining a change of the flow state of a flowable substance importantly contemplates the step of comparing the time duration corresponding to a predetermined number of pseudo periods with a predetermined time duration.

As also mentioned heretofore, the invention is further concerned with apparatus useful for the performance of the aforesaid method, which apparatus contemplates structuring the analyser to possess a detector which always then delivers a detector signal upon the occurrence of a predetermined momentary value of the modulation signal. A pulse generator is arranged following the detector, the pulse generator always then delivering a predetermined pulse upon receiving a detector signal. The analyser further comprises at least one analyser device which is arranged following the pulse generator, the analyser device containing an integrator having charging- and discharging-time constants and a comparator arranged after such integrator. The analyser device serves for the integration of a pulse sequence or train formed of the pulses, for comparing the result of the integration with a predetermined threshold value and for delivering an analyser signal upon the presence of a predetermined result of such comparison.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
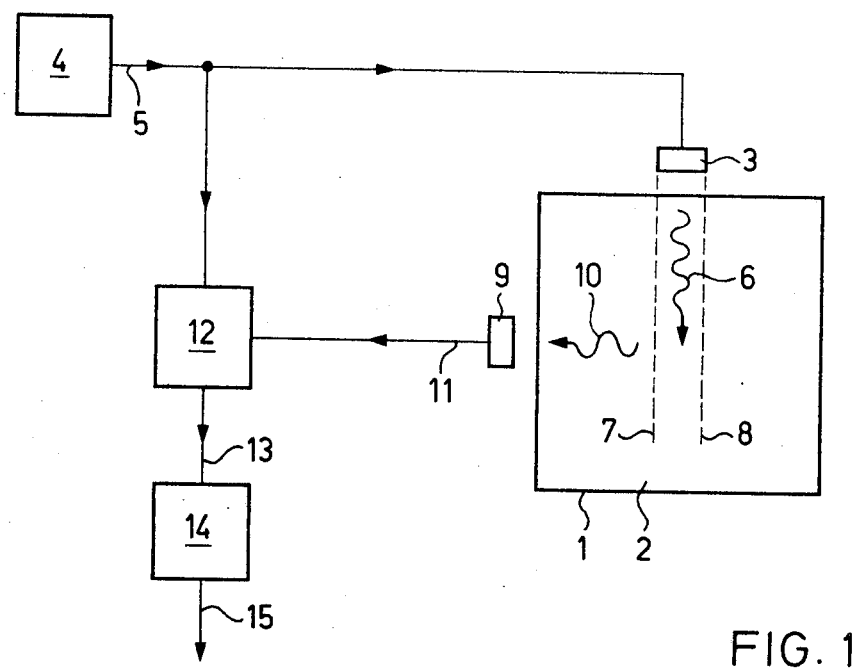
FIG. 1 schematically illustrates a constructional embodiment of apparatus for the determination of the flow state or condition of a substance.

Describing now the drawings, it is to be firstly understood that throughout the various figures there have been generally employed as a matter of convenience the same reference characters to denote the same or equivalent components. Turning specifically to the exemplary embodiment of apparatus for determining a change of the flow state or condition of a flowable or fluent substance, there will be recognized that there is provided a sample container 1 for housing a flowable or fluent substance 2, the flow state of which is to be ascertained. This substance 2 can be for instance whole blood contained in a cuvette or vial or the like, and it can be assumed that there is to be ascertained whether the whole blood is coagulating or coagulated. But of course the teachings of the invention are not limited to blood or like substances, and specifically it is to be understood that the same can also process substances which are flowable but not liquid, for instance fluidized solids employed in the chemical industry in a turbulent bed reactor, where for instance there is to be detected whether the fluidized solids are present, i.e. whether gas and solid particles form a turbulent, microscopic inhomogeneous yet macroscopic homogeneous mixture or whether there has settled a stationary layer of solid particles. Quite generally, there are processed substances possessing microscopic inhomogeneities, the distribution of which, considered macroscopically, can be homogeneous or inhomogeneous or can possess a static state and a moving state.

Continuing, there will be recognized that an ultrasonic transmitter or transducer 3 is arranged at the container 1. A signal generator 4 produces a reference signal of constant frequency for controlling the transmitter 3, the reference signal being delivered to the ultrasonic or ultrasound transmitter 3 by means of a line or conductor 5. The ultrasonic or ultrasound transmitter or transducer 3 produces a beam of ultrasonic waves which have been merely conveniently symbolized by the squiggly or undulated arrow 6, whereas the beam has been symbolically delimited by the broken lines 7 and 8. An ultrasonic or ultrasound receiver 9 is arranged at the container 1 in such a manner that it is impinged by the ultrasonic or ultrasound waves, symbolized by the undulated arrow 10, backscattered by the substance 2, however not by the transmitted ultrasonic waves 6. The ultrasonic receiver 9 delivers a primary signal by means of an output line or conductor 11. The reference signal is thus converted into transmitted ultrasonic waves, and the backscattered ultrasonic waves are converted into the primary signal. The necessary measures for coupling the ultrasonic transmitter or transducer 3 and the receiver 9 with the substance 2 by means of the container 1 are well known in the art and therefore need not be further considered in this disclosure. In the illustrative exemplary embodiment the reference signal and the primary signal are electrical signals, the infeed and outfeed of which requires the use of conventional matching techniques such as impedance transformation or conversion, amplification and the like, which likewise need not be here further considered since these techniques are well known in the electronics art. It is however to be mentioned that the invention is not in principle limited to electrical signals provided that other type of signals or other type of signal transmission can be used, which, for instance, fall into the fields of optical, acoustical or mechanical technology.

As already mentioned, the backscattering of the ultrasonic waves 6 due to the inhomogeneities of the substance 2 is governed by statistical laws: the primary signal is amplitude- and phase-modulated in accordance with the backscattering. If the substance 2 is at a state of rest, i.e. static, then the modulation is equal to null. Of course, when working with a liquid it is necessary to take into account the Brownian motion and convection: particle suspensions, emulsions and the like therefore can cause a modulation of the primary signal even in a "static state", yet such primary signal as concerns its amplitude and frequency possesses a spectrum which differs from the spectrum associated with a moving state of the sample or substance. In order to determine the flow state or condition of the substance 2 there must be carried out a spectral analysis of the modulation of the primary signal. For this purpose initially the modulation of the primary signal is accomplished in a demodulator 12 and appears in the form of a modulation signal at a line or conductor 13. In the described exemplary embodiment, the demodulator 12 is a phase detector to which there is delivered by means of the line 11 the primary signal and by means of a not particularly referenced branched-off portion of the line or conductor 5 the reference signal. A particularly advantageous constructional embodiment of demodulator 12 as a phase detector comprises a dual-gate MOS-FET, which is supplied by a respective signal from the lines or conductors 5 and 11. Such dual-gate MOS-FET circuitry is well known in the art and thus need not be here further considered. It also would be possible to carry out, instead of the here performed phase modulation, an amplitude modulation and to likewise process such obtained signal in a manner as will be considered in the description to follow. The modulation signal delivered at the output of the demodulator 12 to the line or conductor 13 is fed to an analyser 14. In the analyser 14 there is initially determined the time duration needed for a predetermined number of pseudo periods of the modulation signal, this being equivalent to the mean frequency of the spectrum of the modulation signal. Thereafter an analyser signal is supplied to an output line 15 of the analyser 14 when the determined time duration has exceeded a predetermined time duration or, selectively, falls below a predetermined time duration. In conventional manner this can be accomplished by comparison of the counter state of counters for the pseudo periods and the time pulses. However, in the disclosure to follow other particularly favorable constructions will be considered.

Figure 2:
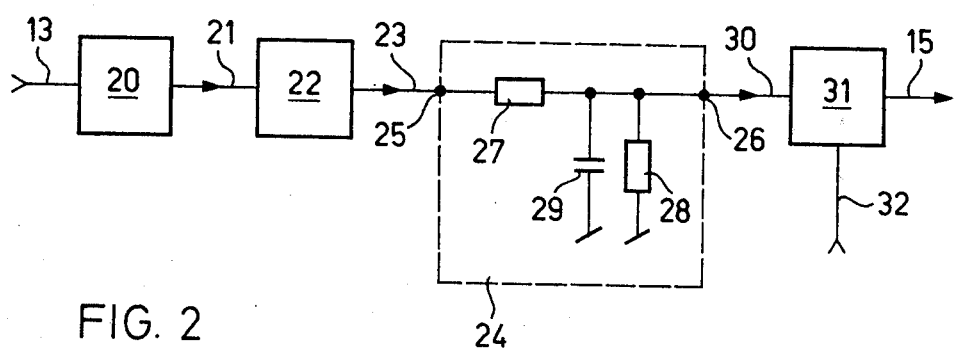
FIG. 2 is a schematic block circuit diagram of the analyser illustrated in the arrangement of FIG. 1.

One particularly favorable constructional embodiment of the analyser 14 of the apparatus of FIG. 1 has been shown in greater detail in FIG. 2 where the lines or conductors 13 and 15 of FIG. 1 have been illustrated. The modulation signal is fed by means of the line 13 to a detector 20 which delivers a detector signal through a line or conductor 21 when the modulation signal has reached a predetermined momentary value. The detector 20 is constructed for instance as a Schmitt-trigger operating as a null value detector, this Schmitt-trigger delivering a detector signal when the modulation signal possesses a null throughpass from a negative to a positive value. In the event that the mean value of the modulation signal is not equal to null, or in the event that the detector signal cannot be produced by a null throughpass of the modulation signal, rather at another value, then the operating point of the Schmitt-trigger can be shifted in conventional manner. There could also be used as the detector 20 a conventional peak value detector in order to produce the detector signal when the modulation signal has reached a maximum or, selectively, a minimum. The detector signal is delivered by the line or conductor 21 to a pulse generator 22 which always then delivers a pulse to a line or conductor 23 when there is infed a detector signal. Both the amplitude as well as the duration of each pulse is predetermined, and thus there is formed a pulse sequence or train of successively identical pulses. The duration of the pulses is selected such that it is much shorter than the duration of the pseudo periods, the presence of which in the modulation signal is to be evaluated. In the case of short pseudo periods there is in fact only detected the presence thereof, the evaluation being saturated thus furnishes a maximum occurrence rate, because the time spacing of the pulses is vanishingly small. In the normal instance, where the spacing between the pulses is considerably greater than the duration of a pulse, the number of pulses produced during a predetermined time duration constitutes a mean value of the frequencies which arise in the frequency spectrum of the modulation signal. The described apparatus also fulfills the purpose of eliminating any effect of the amplitude of the signal components upon the evaluation.

By means of the line or conductor 23 the pulse sequence or train is supplied to an integrator 24 which possesses both a charging-time constant as well as also a self-discharging time constant. In FIG. 2 it is assumed that the signals at one input 25 and at one output 26 of the integrator 24 are both defined with regard to the ground potential. A resistor 27 is connected in circuit between the input 25 and the output 26, while a resistor 28 and a capacitor 29 are connected in parallel between the output 26 and ground. The charging-time constant is equal to the product of the value of the resistor 27 and the capacitor 29, whereas the self-discharging time constant is equal to the product of the value of the resistor 28 and the capacitor 29. Upon infeed of a pulse sequence or train to the integrator 24 there prevails an interaction or reciprocal action between both of the time constants, the momentary and the mean spacing of the pulses. The result of this interaction appears at the output 26 of the integrator 24 in the form of a voltage which is supplied by means of a line 30 to a comparator 31. There is delivered to the comparator 31 a predetermined voltage by means of a line 32, which voltage constitutes a predetermined threshold value. The comparator 31 delivers an analyser signal to the output line or conductor 15 whenever the voltage appearing at the line 30 exceeds or selectively falls below the voltage appearing at the line or conductor 32. This analyser signal serves for the determination of the flow state of the substance 2, as will be more fully explained hereinafter.

Figure 3:
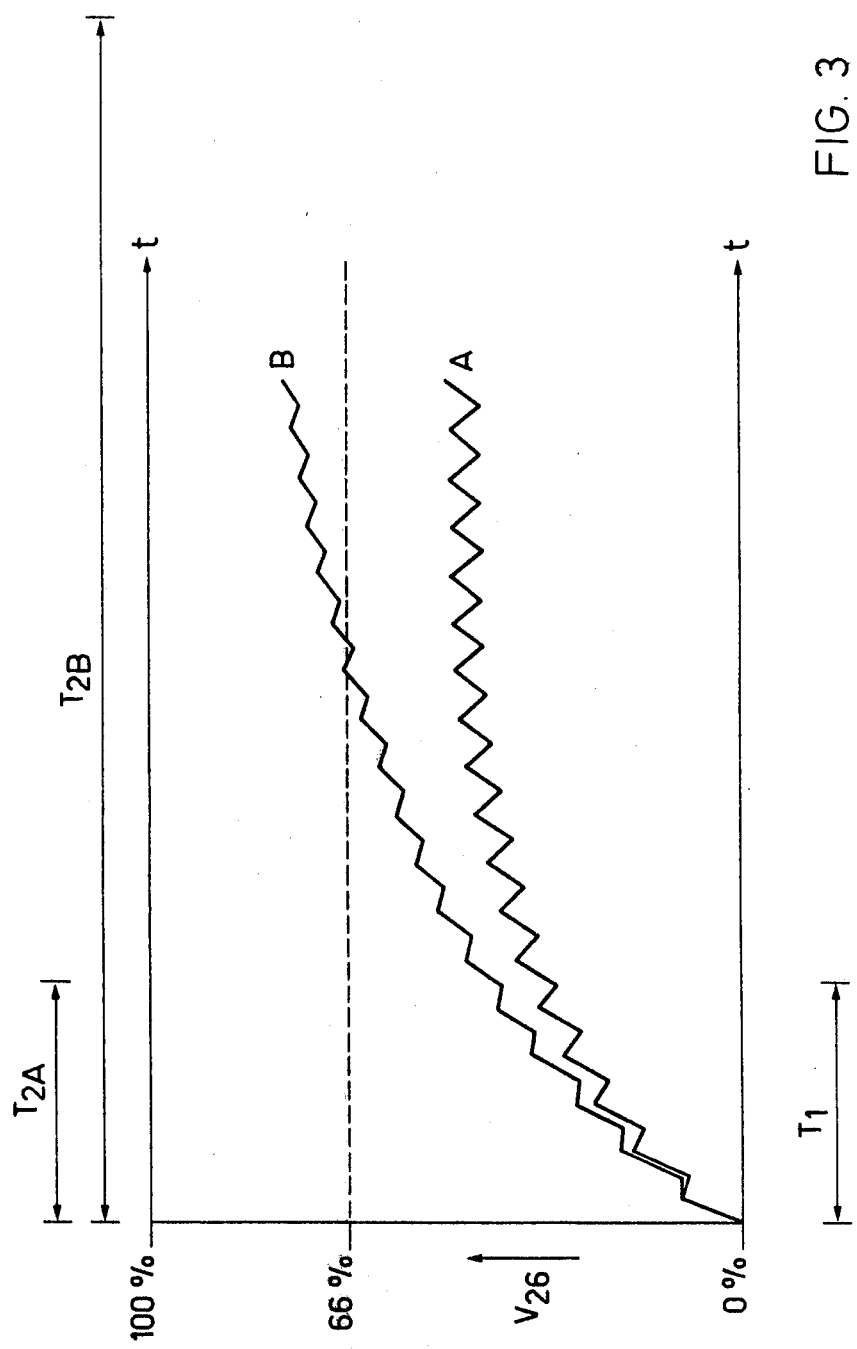
FIG. 3 portrays charge curves of the integrator illustrated in FIG. 2.

In FIG. 3 there is schematically graphically portrayed the course of the voltage $V_{26}$ at the output of the integrator 24 as a function of the time $t$. The charging time constant $T_1$ has been graphically illustrated as well as a respective self-discharging time constant $T_{2A}$ and $T_{2B}$ related to an associated curve A and B respectively. It is assumed that a pulse train is infed to the integrator 24, this pulse train comprising a series of pulses, the amplitude of which is assumed to be equal to a value of 100%, and which furthermore contains during the time constant $T_1$ 5 pulses and 5 pulse pauses or intervals of the same duration $T_1/10$. Such would correspond to a modulation signal which only contains the signal components of the frequency $5/T_1$. It will be apparent that the voltage $V_{26}$ reaches a constant mean or average value during the course of the time, which mean value fluctuates in cycle with the pulses. In the event, as shown, the threshold value is set at 66% of the pulse amplitude, then such threshold value will be exceeded by the curve B after 12 pulses, and will never be exceeded by the curve A. In the case of constant remaining time constants an increase of the repetition frequency of the pulses brings about a shortening of the time sections during which the capacitor 29 can discharge and the voltage $V_{26}$ can drop. Consequently, the capacitor 29 is charged more quickly and the corresponding charging curve is disposed above the curve B. If the pulses follow one another practically without any pulse gaps, then the charging curve transforms into an exponential charging curve. There can be reached and exceeded every predetermined threshold value with the exception of 100%, but then the time needed to do so is predestined and no longer is dependent upon the repetition frequency of the pulses, which has been heretofore designated as saturation. On the other hand, if the repetition frequency of the pulses is lower, the capacitor 29 will be charged more slowly and the corresponding charging curve will be disposed below the curve B. The threshold value of 66% will then be reached at a later time. It can be calculated that with periodically recurring pulses of a pulse duration $T_1/10$ (as shown in FIG. 3) and with the same time constant $T_1$ and $T_{2B}$ as in FIG. 3 the threshold value of 66% is not attainable when the spacing between the pulses becomes greater than approximately $T_{2B}/20$, i.e. when the repetition frequency of the pulses is lower than approximately $2.86/T_1$. Such type conclusion is equally applicable to statistically arriving pulses, provided that the duration of a pulse is considerably shorter than the charging time constant of the integrator and the spacing between the pulses is appreciably shorter than the self-discharging time constant of the integrator, whereby under the term "appreciably", or equivalent terminology, there is to be understood for instance a factor of 100. If these prerequisites are fulfilled then it is possible to reckon with mean values. It is apparent that with the described construction of the analyser 14 the mean repetition period of the pulses can be compared with a part of the self-discharging time constant, which part is governed by the threshold value, and this amounts to nothing other than the comparison of two time intervals. The one time duration is the mean time duration of pseudo periods and can equally be considered as the time duration corresponding to a predetermined number of pseudo periods of the modulation signal, while the other time duration is governed by the selection of the pulse duration and both of the time constants and therefore itself can be considered as predetermined. The determination of a frequency mean value which can be achieved with this construction is indeed not as precise as an actual counting of pseudo periods during a counted-off time, but it is however completely sufficient for the determination of the flow state and can be achieved with extreme equipment economies.

In order to determine the point in time when the substance 2 transforms from a "static state" into a "flow state", the analyser 14 is to be provided with such characteristic values so that by means thereof there can be accomplished exceeding of the threshold value by the charging state of the integrator by relatively high-frequency signal components of the modulation signal, not however by relatively low-frequency signal components. For instance, in the case of whole blood and plasma there can be selected characteristic values for which there are required 50 pulses in 0.5 seconds in order to produce an analyser signal. The static sample liquid then does not produce any analyser signal, whereas an injection of thrombin solution causes turbulence and triggers the analyser signal.

In order to determine the point in time at which the substance 2 transforms from a flow state into a static state, the analyser should be equipped with characteristic values for obtaining the reverse mode of operation or function. With coagulated whole blood or plasma not only does there disappear the turbulence and the convection, but also part of the Brownian movement. If additionally, as described more fully hereinafter, in order to suppress disturbing influences there are suppressed low-frequency signal components below approximately 3 Hz, then the analyser signal should be triggered when no pulse has arrived during a predetermined time duration. For this purpose the integrator is to be provided with a charging time constant which is in the same order of magnitude as the pulse duration, so that each pulse charges the integrator to a value exceeding the threshold value. After the arrival of a pulse the integrator discharges, and if up to the time of exceeding the threshold value there does not arrive any further pulse, then the analyser signal is triggered. The predetermined time duration in this case amounts to the time duration needed for the discharge of the integrator from the charging value to the threshold value, for instance 0.5 seconds. To determine the breakdown of a fluidized solid there is not required any filtering of the modulation signal at 3 Hz, because here the solid particles are either in a turbulent state or form a stationary layer which does not produce any modulation signal.

Figure 4:
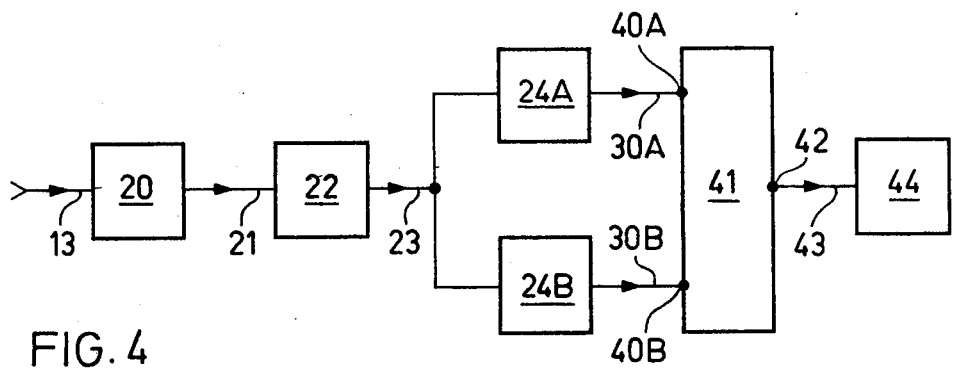
FIG. 4 is a block circuit diagram of a modified embodiment of analyser.

In order to determine the coagulation time of whole blood a time count should be started when the injection of thrombin initiates the coagulation process and at the same time causes a turbulence of the sample liquid, whereas the time count is to be stopped when coagulation has been accomplished and as a result thereof the liquid again brought into a static condition. An advantageous constructional embodiment of appropriate apparatus has been shown in FIG. 4 where the same components or elements 13, 20, 21, 22 and 23 have been illustrated as in the arrangement of FIG. 2. The modulation signal carried by the line or conductor 13, just as was the case for the arrangement of FIG. 2, is delivered to the null value detector 20 which controls, by means of the line 21, the pulse generator 22 during each similar null throughpass of the modulation signal, so that the line or conductor 23 carries a pulse sequence or train which corresponds to the modulation signal. There are provided two integrators 24A and 24B, each of which possess the same structure as the integrator 24 of the arrangement of FIG. 2 previously discussed. However, there are needed approximately 50 pulses in 0.5 seconds in order to charge the integrator 24A to 66% of a pulse amplitude, whereas the integrator 24B can be charged by a single pulse to approximately 63% of the pulse amplitude. Both integrators discharge by about 63% in 1 second. The integrators 24A and 24B are each provided with an output line or conductor 30A and 30B, respectively, which supplies the charging state of the corresponding integrator to a respective input 40A and 40B of a dual or two-fold comparator 41. The comparator 41 is a commercially available component having an output 42. This output 24 does not carry any voltage thereat at the the start of the operation, but at the moment when the voltage infed to the input 40A exceeds a first threshold value of 66% of a pulse amplitude then the output 42 carries a voltage, and specifically for such length of time until the voltage delivered to the input 40B falls below a second threshold value of 33% of a pulse amplitude, whereafter the voltage at the output 42 again drops to null. The voltage at the output 42 forms an analyser signal which is delivered by the line 43 to a time counter 44 and controls the latter. There is measured the time during which a voltage is carried by the line or conductor 43. It will be apparent that the time count starts as soon as approximately 50 pulses have been produced in 0.5 seconds, and the time count terminates when no pulse has been produced in about 0.5 seconds. Both of the time delays of about 0.5 seconds upon starting and stopping the time count extensively compensate one another, and additionally there exists the possibility of delivering to the time counter a correction value which by far enables obtaining the necessary precision of the measuring technique.

Figure 5:
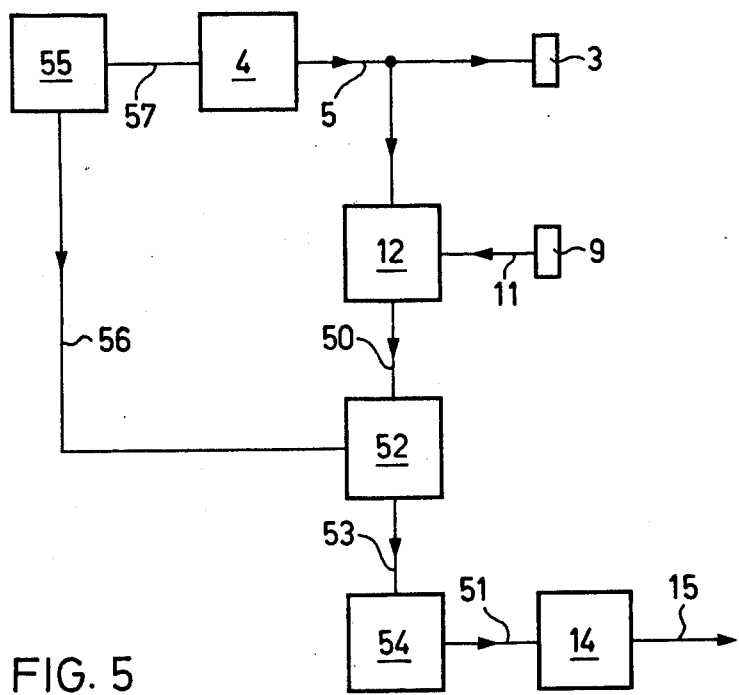
FIG. 5 schematically illustrates a block circuit diagram of a variant embodiment from that shown in FIG. 1.

Finally, in FIG. 5 there is illustrated a constructional variant of the apparatus shown in FIG. 1 having a sampling circuit for the modulation signal. The modulation signal must be sampled when the ultrasonic transmitter or transducer is controlled in its pulse mode or operation, for instance for protecting the transmitter at high intensities or for using the same transducer for transmitting and receiving. Additionally, and as will be apparent from the aforementioned publication, a synchronization of the sampling with the rhythm or cycle of the ultrasound or ultrasonic pulses renders possible a selective evaluation of the backscattering of the ultrasound waves and thus an examination of a predetermined and spatially limited region or specified volume of the substance. In FIG. 5 there have been shown components of the arrangement of FIG. 1. The conductor or line 13 between the phase detector 12 and the analyser 14 is replaced in the arrangement of FIG. 5 by two lines or conductors 50 and 51. The line 50 interconnects the output of the phase detector 12 with an input of a sampling circuit 52 which is conventional in construction and basically functions like a switch which is closed only during short, periodic repetitive time sections and thus connects the line 50 with a line 53. At the line 53 there appears a sequence of sampling values of the phase modulation of the primary signal which is carried by the line 50. This sequence of sampling values is delivered by means of a filter 54 to the line 51 and thus infed to the analyser 14. The sampling frequency, i.e. the rhythm or cycle of the sampling operation, is controlled by a control device 55, which, for this purpose, is connected by means of a line or conductor 56 with the sampling circuit 52. The control device 55 is also furthermore connected by means of a line 57 with the signal generator 4 in order to control such in its pulse mode. In this manner the pulses of the ultrasonic or ultrasound waves are synchronized with the rhythm of the sampling operation in such a manner that the sampling values of the phase modulation correspond to an exactly predetermined transit time of the ultrasonic waves, i.e. a spatially limited region of the substance to be examined. The filter 54 is a bandpass filter which, on the one hand, suppresses the sampling frequency and, on the other hand, suppresses constant remaining, sampling values. For this purpose the bandpass filter 54 is equipped with a respective lower boundary frequency and an upper boundary frequency. For instance, during a pulse mode and a sampling frequency of 2000 Hz the lower boundary frequency can be set at about 3 Hz and the upper boundary frequency at about 300 Hz. There then appears at the line 51, at the output of the filter 54, a modulation signal, the time course of which is an envelope of the sampling values of the phase modulation, and constant or slow changing values are suppressed. The indicated boundary frequencies are especially suitable for the determination of the coagulation time of whole blood. The upper boundary value is high enough in order to ensure for an unambiguous differentiation between the liquid and the coagulated state, whereas it is also low enough in order to eliminate with certainty, with technically acceptable values of the pulse duration and the integrator time constants, a saturation of the evaluation. The lower boundary value is low enough in order to still render possible the detection of the Brownian movement and/or the convection, whereas it is also high enough in order to avoid disturbances in the analysis by external effects, such as slight jarring of the instrument due to movements of the operator, noise from the surroundings or street and the like. Additionally, the suppression of frequencies below the lower boundary value also allows for the suppression of signals which remain constant, caused for instance by echoes at the walls of the container 1 or by electrical crosstalk between the transmitter and the receiver. There are only processed echoes of moving ultrasonic scatterers. The suppression of frequencies below a lower boundary value and the correct setting of this lower boundary value based upon physical findings or knowledge is thus a measure which provides a decisive contribution to the field of application of the method and the apparatus of this development.

While there are shown and described present preferred embodiments of the invention, it is to be distinctly understood that the invention is not limited thereto but may be otherwise variously embodied and practiced within the scope of the following claims.

Accordingly, what we claim is:

1. A method of determining a change of the flow state of a flowable substance, comprising the steps of:
   transmitting ultrasonic waves of substantially constant frequency to a spatial region of the substance;
   receiving ultrasonic waves backscattered by the substance;
   transforming the backscattered ultrasonic waves into a primary signal which is amplitude and phase modulated in accordance with the backscattering;
   demodulating the primary signal to obtain a modulation signal which can be subdivided into a spectrum of signal components of different frequencies and possessing pseudo periods which are defined as the time spacing between successive mutually corresponding momentary values of the signal modulation;
   determining at least one time point at a mean value of the psuedo periods having a monotonous variation with time which entails a monotonous variation with time of the time duration of a predetermined number of pseudo periods;
   comparing a time duration corresponding to a predetermined number of pseudo periods with a predetermined time duration; and wherein
   the time duration of the predetermined number of pseudo periods traverses the predetermined time duration in the course of its monotonous variation with time.

2. The method as defined in claim 1, wherein:
   said step of determining said at least one time point entails determining a first time point at a mean value of the pseudo periods which decreases with time; and wherein,
   the time duration of the predetermined number of pseudo periods is shorter than a first predetermined time duration at said first time point.

3. The method as defined in claim 1, wherein:
   said step of determining at least one time point entails determining a second time point at a mean value of the pseudo periods which increases with time; and wherein,
   at said second time point there are completely absent such pseudo periods, the duration of which is shorter than the reciprocal value of a predetermined boundary frequency during a second predetermined time duration which ends at the second time point.

4. The method as defined in claim 3, wherein:
   said step of determining said at least one time point further entails determining a first time point at a mean value of the pseudo periods which decreases with time and at which first time point the time duration of the predetermined number of pseudo periods is shorter than a first predetermined time duration; and
   starting a time count at the first time point and stopping such time point count at the second time point.

5. The method as defined in claim 4, further including the steps of:
   producing a predetermined pulse whenever there arises a predetermined momentary value of the modulation signal;
   integrating at least one pulse train formed by the pulses while utilizing charging and discharging time constants to produce a result;
   comparing the integration result with a threshold value;
   carrying out two integrations of the same pulse train in parallel;
   starting the time count when the result of the one integration exceeds a first threshold value; and
   stopping the time count when the result of the other integration falls below a second threshold value.

6. The method as defined in claim 1, further including the steps of:
   producing a predetermined pulse whenever there arises a predetermined momentary value of the modulation signal;
   integrating at least one pulse train formed by the pulses while utilizing charging and discharging time constants to produce a result; and wherein,
   the step of comparing said time duration entails comparing the result of the integration with a threshold value.

7. The method as defined in claim 6, wherein:
said predetermined momentary value comprises a null throughpass of the modulation signal.

8. The method as defined in claim 1, wherein:
   the step of demodulating the primary signal entails demodulating the phase values of the primary signal to obtain a phase modulation of the primary signal and
   obtaining a modulation signal corresponding to the phase modulation.

9. The method as defined in claim 8, further including the steps of:
   multiplying the phase modulation with a periodic sampling function of predetermined sampling frequency to obtain a result;
   filtering the result in order to suppress both the sampling frequency and also sampling values which remain constant and to obtain a modulation signal which envelops the sampling values of the phase modulation.

10. The method as defined in claim 9, further including the steps of:
   transmitting the ultrasonic waves in periodically repetitive pulses synchronously with the sampling function.

11. The method as defined in claim 1, further including the steps of:
   utilizing as the substance blood whose coagulation time constitutes the determined change of the flow state thereof.

12. An apparatus for determining a change of the flow state of a flowable substance, comprising:
   a signal generator for producing a reference signal of substantially constant frequency;
   said signal generator having an output side;
   an ultrasonic transmitter arranged in circuit with the output side of the signal generator for transmitting ultrasonic waves corresponding to the reference signal to a spatial region of the substance;
   an ultrasonic receiver for receiving ultrasonic waves which are backscattered at the substance and for converting such backscattered ultrasonic waves into a primary signal which is amplitude and phase modulated in accordance with the backscattering;
   a demodulator for obtaining a modulation signal from said primary signal;
   an analyser for detecting signal components of the modulation signal;
   said analyser being structured to comprise a detector which delivers a detector signal upon the presence of a predetermined momentary value of the modulation signal;
   said detector having an output side;
   a pulse generator connected with the output side of said detector;
   said pulse generator delivering a predetermined pulse upon reception of a detector signal;
   said pulse generator having an output side;
   said analyser further comprising at least one analysis device connected in circuit with the output side of said pulse generator;
   said analysis device comprising an integrator having an output side and possessing charging and discharging time constants and a comparator connected at the ouput side of the integrator; and
   said analysis device serving for the integration of a pulse train formed from the pulses, for the comparison of the result of the integration with a predetermined threshold value and for delivering an analysis signal upon the presence of a predetermined result of the comparison.

13. The apparatus as defined in claim 12, wherein:
said analyser comprises two of said analysis devices; and
time counter means arranged at the output side of the associated comparators of the analysis devices.

14. The apparatus as defined in claim 12, wherein:
said detector is structured as a null value detector for determining a null throughpass of the modulation signal.

15. The apparatus as defined in claim 12, wherein:
   said demodulator comprises a phase detector having two inputs and an output;
   one of the inputs serving for the infeed of the reference signal and the other input for the infeed of the primary signal;
   said output of the phase detector serving for the outfeed of the modulation signal which corresponds to the phase modulation of the primary signal.

16. The apparatus as defined in claim 15, further including:
   a sampling circuit arranged at the output side of the phase detector;
   said sampling circuit having a predetemined sampling frequency;
   bandpass filter means arranged at the output side of the sampling circuit for suppressing both the sampling frequency and sampling values which remain substantially constant and for delivering a modulation signal enveloping the sampling values of the phase modulation at an output of the demodulator.

17. The apparatus as defined in claim 15, further including:
   control means arranged in circuit with and ahead of the signal generator and the sampling circuit for producing a pulse operation of the signal generator which is synchronized with the sampling frequency.

18. An apparatus for determining a change of the flow state of a flowable substance, comprising:
   a signal generator for producing a reference signal of substantially constant frequency;
   said signal generator having an output side;
   an ultrasonic transmitter arranged in circuit with the output side of the signal generator for transmitting ultrasonic waves corresponding to the reference signal to a predetermined region of the substance;
   an ultrasonic receiver for receiving ultrasonic waves which are backscattered at the substance and for converting such backscattered ultrasonic waves into a primary signal which is modulated in accordance with the backscattering;
   a demodulator for obtaining a modulation signal from said primary signal;

an analyser for detecting signal components of the modulation signal;

said analyser comprising a detector which delivers a detector signal upon the presence of a predetermined momentary value of the modulation signal;

said detector having an output side;

a pulse generator connected with the output side of said detector;

said pulse generator delivering a predetermined pulse upon reception of a detector signal;

said pulse generator having an output side;

said analyser further comprising at least one analysis device connected in circuit with the output side of said pulse generator;

said analysis device containing an integrator having charging and discharging time constants and a comparator connected to the output side of the integrator; and said analysis device serving for the integration of a pulse train formed from the pulses, for the comparison of the result of the integration with a predetermined threshold value and for delivering an analysis signal upon the presence of a predetermined result of the comparison.

* * * * *